(12) United States Patent
Hawthorne et al.

(10) Patent No.: US 6,969,350 B1
(45) Date of Patent: Nov. 29, 2005

(54) BODY FAT MEASUREMENT SYSTEM

(75) Inventors: Amanda Jane Hawthorne, Langar (GB); Richard Bradley, Grantham (GB); Richard Fulton Butterwick, West Bridgford (GB)

(73) Assignee: Mars U.K. Limited, Slough (GB)

( * ) Notice: Subject to any disclaimer, the term of this patent is extended or adjusted under 35 U.S.C. 154(b) by 0 days.

(21) Appl. No.: 09/831,733

(22) PCT Filed: Nov. 12, 1999

(86) PCT No.: PCT/GB99/03775

§ 371 (c)(1), (2), (4) Date: Apr. 3, 2002

(87) PCT Pub. No.: WO00/28897

PCT Pub. Date: May 25, 2000

(30) Foreign Application Priority Data

| | | | |
|---|---|---|---|
| Nov. 13, 1998 | (GB) | ................................... | 9824976 |
| Jan. 7, 1999 | (GB) | ................................... | 9900296 |

(51) Int. Cl.$^7$ ............................................. A61B 5/00
(52) U.S. Cl. ...................... 600/300; 128/898; 128/920
(58) Field of Search ................................ 600/587, 300; 128/897, 898, 920, 921

(56) References Cited

U.S. PATENT DOCUMENTS

| | | |
|---|---|---|
| 4,127,112 A | 11/1978 | Sherlock et al. |
| 5,372,141 A | 12/1994 | Gallup et al. |

FOREIGN PATENT DOCUMENTS

| | | |
|---|---|---|
| CA | 2123542 | 11/1994 |
| EP | 0 940 120 A1 | 9/1999 |
| FR | 2 731 144 | 9/1996 |
| GB | 858738 | 1/1961 |
| GB | 2 213 936 A | 8/1989 |
| GB | 2 220 752 A | 1/1990 |
| JP | 10-192258 | 7/1998 |
| WO | WO 98/08437 | 3/1998 |

OTHER PUBLICATIONS

Gresham JD, et al., "Prediction of mature cow carcass composition from live animal measurements," Journal of Animal Science, vol. 63(4), Oct. 1986, pp. 1041-1048.*

Stanton CA, et al., "Bioelectrical impedance and zoometry for body composition analysis in domestic cats," American Journal of Veterinary Research, vol. 53, No. 2, Feb. 1992, pp. 251-257.*

Lefebvre C, et al. "Prediction of body compositions of live and post-mortem red foxes," Journal of Wildlife Diseases, vol. 35, No. 2, 1999, pp. 161-170.*

E. C. Rush, et al., "Estimation of Body Fat in Caucasian and Polynesian Women from Anthropometric Measurements", Appl. Radiat. Isot. (1998), vol. 49, No. 56, pp. 749-750.

* cited by examiner

Primary Examiner—Eric F. Winakur
(74) Attorney, Agent, or Firm—Fitzpatrick, Cella, Harper & Scinto

(57) ABSTRACT

A body fat measurement system for mammals includes means for measuring first and second body dimensions having a high correlation with body fat and low correlation respectively. A lookup table provides an output of the percentage body fat on input of the first and second dimensions.

12 Claims, 5 Drawing Sheets

Figure 1:
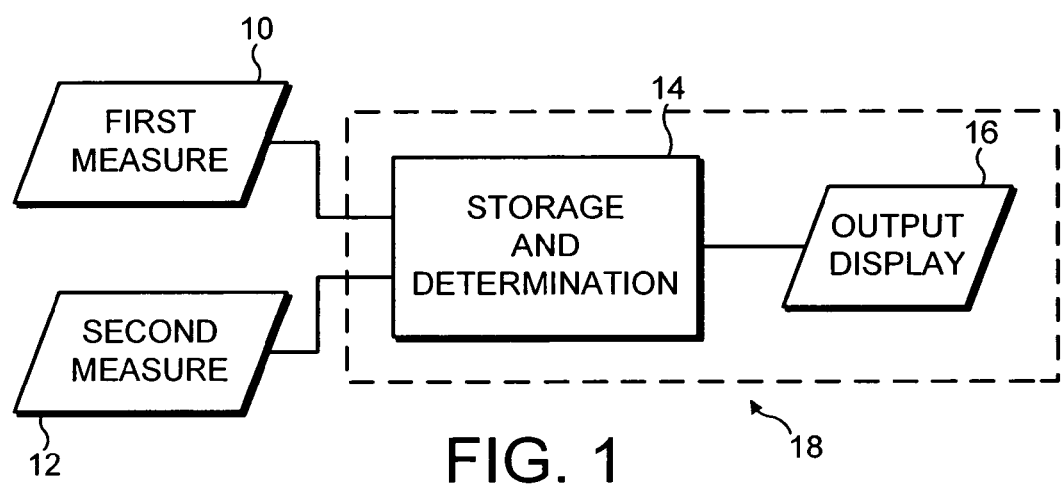

FIG. 4
'IDEAL' BODY WEIGHT (kg)

| | | BODY WEIGHT KG | | | | | | | | | | | | | |
|---|---|---|---|---|---|---|---|---|---|---|---|---|---|---|---|
| % FAT | | 3 | 3.5 | 4 | 4.5 | 5 | 5.5 | 6 | 6.5 | 7 | 7.5 | 8 | 8.5 | 9 | 9.5 | 10 |
| | 10 | 3.6 | 4.2 | 4.8 | 5.4 | 6 | 6.6 | 7.2 | 7.8 | 8.4 | 9 | 9.6 | 10.2 | 10.8 | 11.4 | 12 |
| | 15 | 3.4 | 4 | 4.5 | 5.1 | 5.7 | 6.2 | 6.8 | 7.3 | 7.9 | 8.5 | 9 | 9.6 | 10.2 | 10.7 | 11.3 |
| | 20 | 3.2 | 3.7 | 4.3 | 4.8 | 5.3 | 5.9 | 6.4 | 6.9 | 7.4 | 8 | 8.5 | 9 | 9.6 | 10.1 | 10.6 |
| | 25 | 3 | 3.5 | 4 | 4.5 | 5 | 5.5 | 6 | 6.5 | 7 | 7.5 | 8 | 8.5 | 9 | 9.5 | 10 |
| | 30 | 2.8 | 3.3 | 3.7 | 4.2 | 4.7 | 5.1 | 5.6 | 6.1 | 6.5 | 7 | 7.4 | 7.9 | 8.4 | 8.8 | 9.3 |
| | 35 | 2.6 | 3 | 3.5 | 3.9 | 4.3 | 4.8 | 5.2 | 5.6 | 6.1 | 6.5 | 6.9 | 7.3 | 7.8 | 8.2 | 8.6 |
| | 40 | 2.4 | 2.8 | 3.2 | 3.6 | 4 | 4.4 | 4.8 | 5.2 | 5.6 | 6 | 6.4 | 6.8 | 7.2 | 7.6 | 8 |
| | 45 | 2.2 | 2.6 | 2.9 | 3.3 | 3.7 | 4 | 4.4 | 4.8 | 5.1 | 5.5 | 5.9 | 6.2 | 6.6 | 6.9 | 7.3 |
| | 50 | 2 | 2.3 | 2.7 | 3 | 3.3 | 3.7 | 4 | 4.3 | 4.7 | 5 | 5.3 | 5.7 | 6 | 6.3 | 6.6 |
| | 55 | 1.8 | 2.1 | 2.4 | 2.7 | 3 | 3.3 | 3.6 | 3.9 | 4.2 | 4.5 | 4.8 | 5.1 | 5.4 | 5.7 | 6 |
| | 60 | 1.6 | 1.9 | 2.2 | 2.4 | 2.7 | 2.9 | 3.2 | 3.5 | 3.7 | 4 | 4.3 | 4.5 | 4.8 | 5.1 | 5.3 |

FIG. 5
DAILY ENERGY ALLOWANCE FOR A CAT WITH LOW ACTIVITY (50kcal/kg 'IDEAL' WEIGHT)

| | | BODY WEIGHT KG | | | | | | | | | | | | | |
|---|---|---|---|---|---|---|---|---|---|---|---|---|---|---|---|
| % FAT | | 3 | 3.5 | 4 | 4.5 | 5 | 5.5 | 6 | 6.5 | 7 | 7.5 | 8 | 8.5 | 9 | 9.5 | 10 |
| | 10 | 251 | 293 | 335 | 377 | 419 | 461 | 503 | 545 | 587 | 628 | 670 | 712 | 754 | 796 | 838 |
| | 15 | 237 | 277 | 317 | 356 | 396 | 435 | 475 | 514 | 554 | 594 | 633 | 673 | 712 | 752 | 791 |
| | 20 | 223 | 261 | 298 | 335 | 372 | 410 | 447 | 484 | 521 | 559 | 596 | 633 | 670 | 708 | 745 |
| | 25 | 209 | 244 | 279 | 314 | 349 | 384 | 419 | 454 | 489 | 524 | 559 | 594 | 628 | 663 | 698 |
| | 30 | 196 | 228 | 261 | 293 | 326 | 358 | 391 | 424 | 456 | 489 | 521 | 554 | 587 | 619 | 652 |
| | 35 | 182 | 212 | 242 | 272 | 303 | 333 | 363 | 393 | 424 | 454 | 484 | 514 | 545 | 575 | 605 |
| | 40 | 168 | 196 | 223 | 251 | 279 | 307 | 335 | 363 | 391 | 419 | 447 | 475 | 503 | 531 | 559 |
| | 45 | 154 | 179 | 205 | 230 | 256 | 282 | 307 | 333 | 358 | 384 | 410 | 435 | 461 | 486 | 512 |
| | 50 | 140 | 163 | 186 | 209 | 233 | 256 | 279 | 303 | 326 | 349 | 372 | 396 | 419 | 442 | 465 |
| | 55 | 126 | 147 | 168 | 189 | 209 | 230 | 251 | 272 | 293 | 314 | 335 | 356 | 377 | 398 | 419 |
| | 60 | 112 | 130 | 149 | 168 | 186 | 205 | 223 | 242 | 261 | 279 | 298 | 317 | 335 | 354 | 372 |

FIG. 6
DAILY ENERGY ALLOWANCE FOR A CAT WITH NORMAL ACTIVITY (70kcal/kg 'IDEAL' WEIGHT)

| | BODY WEIGHT KG | | | | | | | | | | | | | | | |
|---|---|---|---|---|---|---|---|---|---|---|---|---|---|---|---|---|
| % FAT | | 3 | 3.5 | 4 | 4.5 | 5 | 5.5 | 6 | 6.5 | 7 | 7.5 | 8 | 8.5 | 9 | 9.5 | 10 |
| | 10 | 251 | 293 | 335 | 377 | 419 | 461 | 503 | 545 | 587 | 628 | 670 | 712 | 754 | 796 | 838 |
| | 15 | 237 | 277 | 317 | 356 | 396 | 435 | 475 | 514 | 554 | 594 | 633 | 673 | 712 | 752 | 791 |
| | 20 | 223 | 261 | 298 | 335 | 372 | 410 | 447 | 484 | 521 | 559 | 596 | 633 | 670 | 708 | 745 |
| | 25 | 209 | 244 | 279 | 314 | 349 | 384 | 419 | 454 | 489 | 524 | 559 | 594 | 628 | 663 | 698 |
| | 30 | 196 | 228 | 261 | 293 | 326 | 356 | 391 | 424 | 456 | 489 | 521 | 554 | 587 | 619 | 652 |
| | 35 | 182 | 212 | 242 | 272 | 303 | 333 | 363 | 393 | 424 | 454 | 484 | 514 | 545 | 575 | 605 |
| | 40 | 168 | 196 | 223 | 251 | 279 | 307 | 335 | 363 | 391 | 419 | 447 | 475 | 503 | 531 | 559 |
| | 45 | 154 | 179 | 205 | 230 | 256 | 282 | 307 | 333 | 358 | 384 | 410 | 435 | 461 | 486 | 512 |
| | 50 | 140 | 163 | 186 | 209 | 233 | 256 | 279 | 303 | 326 | 349 | 372 | 396 | 419 | 442 | 465 |
| | 55 | 128 | 147 | 168 | 189 | 209 | 230 | 251 | 272 | 293 | 314 | 335 | 356 | 377 | 398 | 419 |
| | 60 | 112 | 130 | 149 | 168 | 186 | 205 | 223 | 242 | 261 | 279 | 298 | 317 | 335 | 354 | 372 |

FIG. 7
DAILY ENERGY ALLOWANCE FOR WEIGHT LOSS (60% OF PREDICTED ER AT TARGET BODY WEIGHT, WHERE ER IS CONSIDERED TO BE 60kcal/kg IDEAL WT)

| | BODY WEIGHT KG | | | | | | | | | | | | | | | |
|---|---|---|---|---|---|---|---|---|---|---|---|---|---|---|---|---|
| % FAT | | 3 | 3.5 | 4 | 4.5 | 5 | 5.5 | 6 | 6.5 | 7 | 7.5 | 8 | 8.5 | 9 | 9.5 | 10 |
| | 10 | 129 | 151 | 172 | 194 | 215 | 237 | 259 | 280 | 302 | 323 | 345 | 366 | 388 | 409 | 431 |
| | 15 | 122 | 142 | 163 | 183 | 203 | 224 | 244 | 265 | 285 | 305 | 326 | 346 | 366 | 387 | 407 |
| | 20 | 115 | 134 | 153 | 172 | 192 | 211 | 230 | 249 | 268 | 287 | 306 | 326 | 345 | 364 | 383 |
| | 25 | 108 | 126 | 144 | 162 | 180 | 198 | 215 | 233 | 251 | 269 | 287 | 305 | 323 | 341 | 359 |
| | 30 | 101 | 117 | 134 | 151 | 168 | 184 | 201 | 218 | 235 | 251 | 268 | 285 | 302 | 318 | 335 |
| | 35 | 93 | 109 | 124 | 140 | 156 | 171 | 187 | 202 | 218 | 233 | 249 | 265 | 280 | 296 | 311 |
| | 40 | 86 | 101 | 115 | 129 | 144 | 158 | 172 | 187 | 201 | 215 | 230 | 244 | 259 | 273 | 287 |
| | 45 | 79 | 92 | 105 | 119 | 132 | 145 | 158 | 171 | 184 | 198 | 211 | 224 | 237 | 250 | 263 |
| | 50 | 72 | 84 | 96 | 108 | 120 | 132 | 144 | 156 | 168 | 180 | 192 | 203 | 215 | 227 | 239 |
| | 55 | 65 | 75 | 86 | 97 | 108 | 119 | 129 | 140 | 151 | 162 | 172 | 183 | 194 | 205 | 215 |
| | 60 | 57 | 67 | 77 | 86 | 96 | 105 | 115 | 124 | 134 | 144 | 153 | 163 | 172 | 182 | 192 |

BODY FAT MEASUREMENT SYSTEM

The present invention relates to a system for measurement of the percentage of body fat by weight of four legged mammals, in particular four legged domestic pet mammals such as domestic cats.

Obesity is the most common form of malnutrition in cats, however, the links between obesity and the risk of clinical conditions are not well understood. This is primarily because there is no accepted method for defining obesity or measuring body fat in cats.

The body mass index (BMI), which is based only upon measurements of body weight and height, allows objective measurement available for humans. The main techniques available to veterinary practitioners are subjective ones is such as the Body Condition Score (BCS) system produced by Laflamme.

We have appreciated the requirement for a simple, objective system for determining the percentage body fat by weight of four legged domestic pet mammals, in particular cats. In particular, we have appreciated that the system should be reliable and capable of implementation in both technologically simple and complex embodiments. The system should also be easy for inexperienced operators to use.

Accordingly, there is provided a four legged domestic pet mammal body fat determining system for determining the percentage body fat of a four legged domestic pet mammal, comprising:
means for measuring a first body dimension having a high correlation with percentage body fat;
means for measuring a second body dimension having a low correlation with percentage body fat; and
a look-up table comprising a first storage area for storing entries of the first body dimension, a second storage area for storing entries of the second body dimension and an output area for indicating the percentage body fat determined from a relationship between the first and second body measurements.

The system of the invention has the advantages of being simple to operate, reliable and capable of implementation as a low technological manual system, or a more sophisticated computerised implementation.

In a preferred embodiment the first body dimension is the circumference of the ribcage. This measurement has been appreciated, through experimentation, to be highly correlated to a four legged mammal's percentage body fat. In the embodiment, the second body dimension is a leg index measurement, preferably the distance between the Patella (knee) and the calcaneal tuber (hock) with the leg flexed of the hind limb which, we have appreciated, has a low correlation with percentage body fat. The use of the body measurement of high correlation with body fat and one with low correlation increases the accuracy of the determined percentage body fat.

We have also appreciated the difficulties in providing a correct energy allowance for four legged domestic pet mammals such as cats.

Feeding guides for cats are based on an understanding of their daily energy requirement. A precise understanding of the energy requirement of the cat is therefore fundamental for the development of accurate feeding guides. If the predicted energy requirement of a cat is lower than the actual energy needs then the feeding guide will not provide sufficient energy. On the other hand if the estimated energy requirement for a cat overestimates the actual energy needs then the feeding guide will provide too much energy which can potentially cause the animal to become overweight.

We have also appreciated that a system for measuring percentage body fat can be used to provide a system for determining the energy requirement and ideal weight of a four legged mammal, such as a cat.

Accordingly, there is also provided a four legged domestic pet mammal target body weight determining system for determining a target body weight for a four legged mammal, comprising: a system for measuring the percentage body fat of a four legged domestic pet mammal; and a lookup table comprising a first storage area for storing entries of the percentage body fat, a second storage area for storing entries of body weight, and an output storage area storing an indication of the target body weight. The preferred embodiment also comprises a system for determining the energy requirement based on the ideal weight.

A system embodying the invention will now be described with reference to the accompanying figures in which:—

Figure 2:
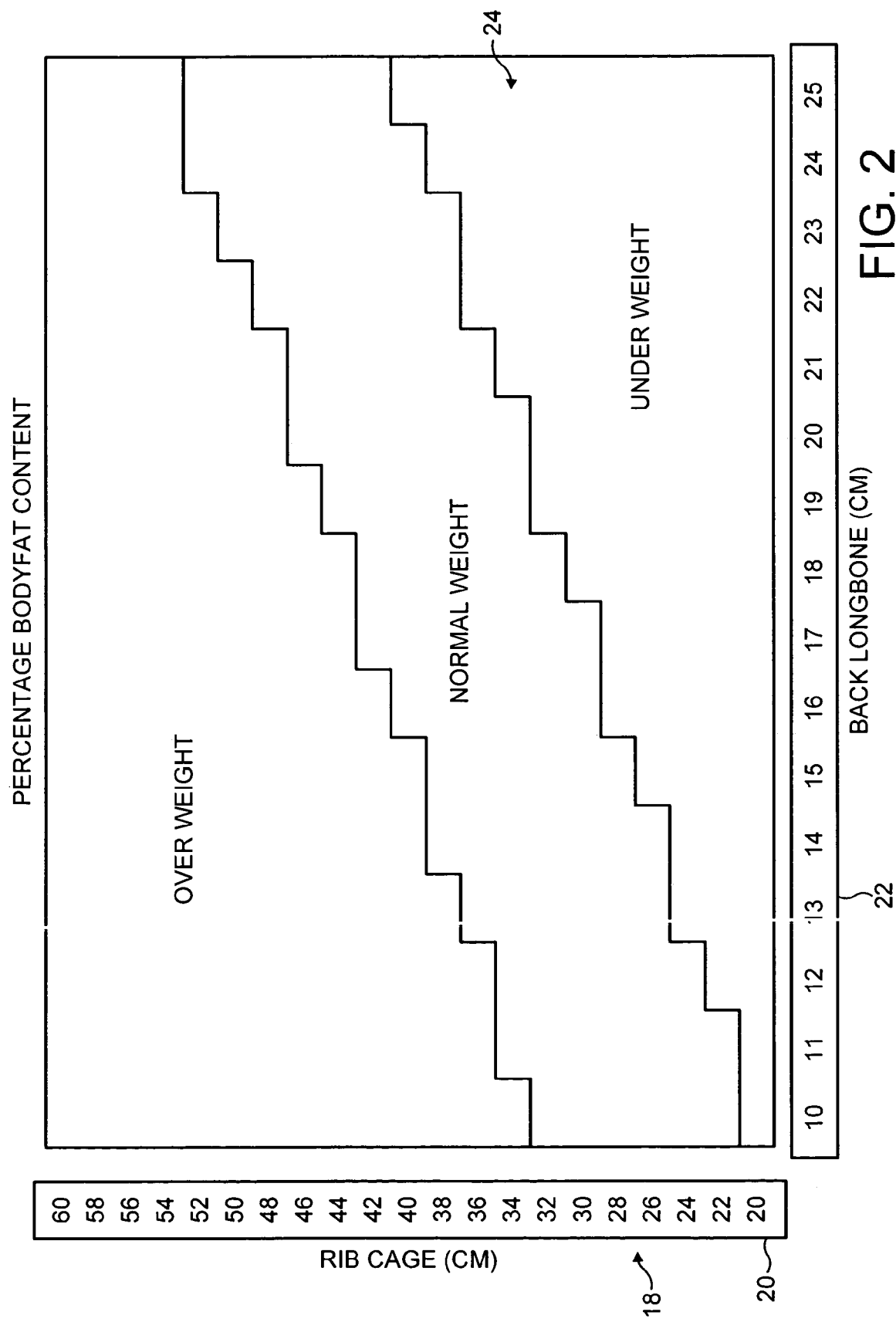
Figure 3:
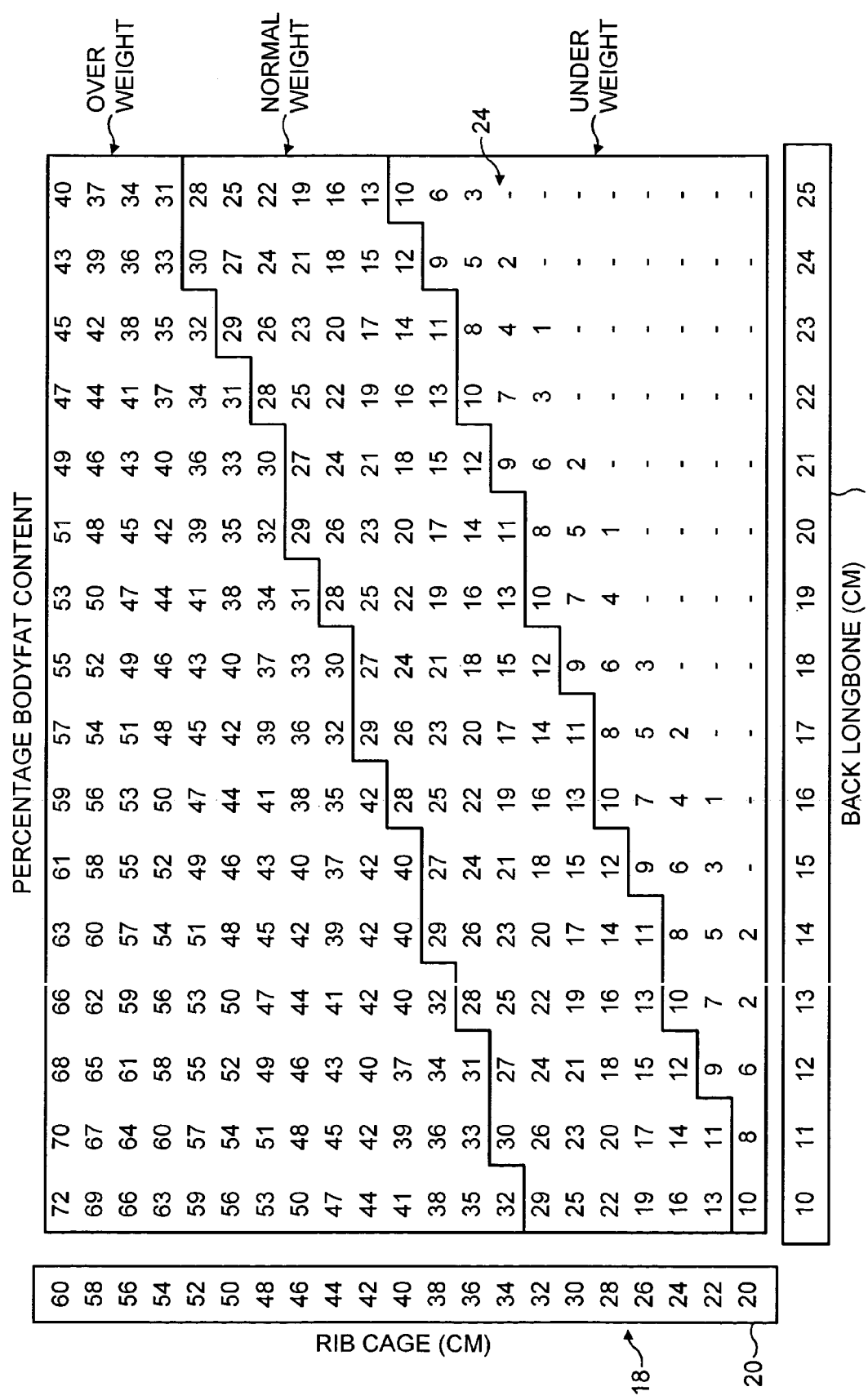

FIG. 1—is a diagrammatic representation of a system embodying the invention;

FIG. 2—is a diagrammatic representation of a first look-up table for use in the system of FIG. 1;

FIG. 3—is a diagrammatic representation of a second look-up table for use in the system of FIG. 1;

FIG. 4—is a diagrammatic representation of a third look-up table;

FIG. 5—is a diagrammatic representation of a fourth look-up table;

FIG. 6—is a diagrammatic representation of a fifth look-up table; and

FIG. 7—is a diagrammatic representation of a sixth look-up table.

The embodiment shown in FIG. 1 may be either manually operated, or a computerised system. A first measurement device 10 and a second measurement device 12 are provided to take measurements of, respectively, the ribcage circumference and the leg index measurement [LIM] to provide the results to the look-up table 18. In a computerised embodiment, the measurement devices 10, 12 would provide measurement signals to a computer, storing therein in first, second and output storage areas respectively, ribcage and LIM, and corresponding fat percentage indications. These are shown as storage and determination functions 14 in FIG. 1. The results are displayed as an output display 16. The determination algorithm (described later) could be coded in any simple computer language, and is within the common general knowledge of the skilled person, and need not be described here.

A manual representation of the look-up table 18 is shown in FIGS. 2 and 3. There is shown a first storage area 20, storing first body dimensions (ribcage) measurements, and a second storage area 22, storing second body dimensions (LIM). An output storage area 24 stores an indication of the percentage body fat of a domestic cat as a relationship of the first and second dimensions. The indication is under, normal or overweight in FIG. 2. In FIG. 3, the indication is given as a percentage number.

In appreciating that the system embodying the invention provides a uniquely robust and reliable system for determining the percentage body fat of a cat, a number of experiments were undertaken, as will now be described.

To establish the correlation between body condition score (BCS) and body composition (% body fat) as measured using Dual Energy X-Ray Absorptiometry (DXA), and to compare zoometric measurements with estimates of body condition score and % body fat using DXA, in order to develop a simple objective method of determining body condition, the following method was adopted.

Zoometric measurements and estimates of BCS (body condition score) and body composition (using DXA), were take from 60 domestic, short-haired cats, housed indoors. All measurements were taken between Mar. 3, 1997 and 22 May 1997, by a single observer. In the study, 28 males (all neutered) and 32 females (of which 8 were entire) were used. The average age of the females was 4.92 years and males 3.94 years. The body weights of entire female cats ranged from 2.34 to 4.1 Kg, the neutered female cats from 2.84 to 6.6 Kg and the males 4.2 to 8.18 Kg. Cats had been fed a variety of diets at the time measurements were taken.

The following zoometric measurements were taken from each cat. These were selected because they were considered to represent body condition or had been found from human data to be potentially useful.

Height: The distance between the ground and the Withers (the top of the shoulder blade or scapula) as measured using a measuring stick. This is a wooden meter ruler with a fixed base, perpendicular to the rule and a sliding wooden bar.

Chest Dept: The vertical distance from the top of the capula to the bottom of the chest, using a measuring stick.

Girth: The circumference at the point of the 4th lumbar vertebrae, just behind the last rib, using a measuring tape.

Ribcage: The circumference at the point of the 9th rib (5 ribs from the posterior end of the ribcage), using a tape measure.

Length: The horizontal distance from the breast-bone (manubrium) to the thigh perineum), using a measuring stick.

Elbow: Measured on the left elbow using a calliper. It is the distance between the lateral epicondyle of the humerus and the medial epicondyle of the humerus.

Front Long Bone; The length of the humerus, from the proximal ulnar epiphysis to the distal radial epiphysis, using a measuring stick.

Leg index measurement [LIM]: The distance between the Patella (knee) and the calcaneal tuber (hock) with the leg flexed.

All measurements were taken from the left hand side of the cat whilst it was standing with its legs perpendicular to the ground and with its head up and looking forward. Cats were weighed prior to taking the measurements, which were taken in a fasted state. Five replicates of each measurement were taken on the same day.

The Purina Body Condition Score (Laflamme, 1998) was used as a subjective assessment of body condition. The cat was given a score on a nine point scale, which ranged from 1 for emaciated to 9 for morbidly/grossly obese, although experienced assessors are able to grade cats to 0.5 of a scale. A cat with a BCS score of 5 was considered to be ideal. This scoring system was based on a variety of features, which included palpability of the ribs, presence of a discernible waist and abdominal tuck, and evidence of bony prominence and fat deposits on the lumbar area and base of the tail.

The percentage body fat was measured by dual energy X-ray absorptiometry, using a Hologic QDR 1000/W densitometer. They were anaesthetised using Domitor (0.1 ml/Kg) and recovery induced with Antisepen.

Eight inexperienced observers each made an estimate of BCS and took their replicates of each zoometric measurement on the same seven cats, in order to test for inter-observer variability in predicting body condition.

Each Zoometric measurement was compared with % body fat because this represented the most objective estimate of body composition. The most significant correlation with % body fat was for ribcage. This factor is more likely to be affected by an increase in body weight or obesity. It may therefore be considered to provide an estimate of % body fat, or 'fatness'. The lowest correlation's with % body fat were found for the LIM and height measurements ($r^2$ <15.4%). This is a low correlation. These may therefore be considered to be measurements of stature which are relatively unaffected by changes in % body fat.

We appreciated that a system could be devised using this data to provide a simple system for measuring the percentage body fat of cats. The formula that describes the most variation in percentage body fat and is biologically meaningful is:

$$Fat = \left[ \frac{\left( \frac{Ribcage}{0.7067} - LIM \right)}{0.9156} \right] - LIM$$

The mean, standard deviation and coefficient of variation were determined for each of the 60 cats from the five replicates made for each zoometric measurement by the experienced observer. The mean and median coefficient of variation (CV) for each zoometric measurement was less than 10% suggesting that the intra-observer repeatability was low and that a single measurement would be needed in future (see table below).

CV for each zoometric measurement made by a single experienced assessor.

| | Coefficient of Variation (%) | | | |
| --- | --- | --- | --- | --- |
| | Mean | Median | Min | Max |
| Weight | 2.30 | 1.19 | 0 | 12.78 |
| Girth | 1.96 | 1.57 | 0.27 | 6.74 |
| Ribcage | 3.03 | 2.6 | 0.5 | 15.57 |
| Height | 1.49 | 0.93 | 0.18 | 8.94 |
| Chest Dept | 3.54 | 3.34 | 1.36 | 9.62 |
| Length | 2.37 | 2.15 | 0.22 | 6.26 |
| Elbow | 4.28 | 4.35 | 0 | 9.56 |
| Front Long Bone | 2.11 | 1.77 | 0 | 5.26 |
| LIM | 2.5 | 2.16 | 0.33 | 8.19 |

The cats included in this study encompassed a wide range of body composition and age, but were of a single population of related genetic domestic short-haired stock. They may therefore form a representative sub-sample of the domestic cat population in general.

BCS was significantly correlated with % body fat, when measured using DXA ($r^2$=73.4%, p<0.01) and gave a reasonable prediction of % fat. However, the correlation was lower than that reported by Laflamme (1998) where $r^2$ = 83.5%, although 48 cats were used in this study, of which only 4 individuals had a BCS less than 5. Using the BCS system in this study, cats which were of ideal body condition (BCS=5) had between 15 and 30% body fat. Cats which were considered to be underweight (BCS<5), were less than 20% fat and those which were overweight (BCS>6) were more than 30% fat. Whilst these data sets are relatively small (underweight group=7 cats, ideal=8 cats) it gives an indication of the cut off points that might be used for these major categories of % body fat for cats. The largest discrepancy between % body fat and BCS occurred for those animals considered to have a BCS between 5 and 6. This may indicate the problems of correctly identifying animals of 'ideal' condition when animals differed greatly in stature. Animal stature, particularly of very large or small cats was considered to be a determining factor in the large variation of BCS assigned to individual cats by different observers, resulting in a relatively high CV of 15.3%. It would appear that the BCS type of assessment is truly subjective.

By comparison zoometric measurements, and ribcage in particular ($r^2$=82.9%) were more highly correlated with % body fat than the BCS system. This is a high correlation.

The high level of repeatability for the ribcage and LIM measurements of cats and the high correlation between the zoometric model and % body fat suggests that this objective measurement is a more appropriate tool for determining body composition of cats than BCS. In addition it is also non-invasive, requires little training to achieve an acceptable level of repeatability and requires only a metric tape measure. This makes this method available for all veterinary practitioners and cat owners.

Feeding guides for cats are currently formulated on the basis that daily energy requirements are a function of body weight i.e. energy requirement (kcal/day)=70×BW (kg). Different levels of activity (for a given body weight) can be accounted for by using a sliding scale i.e. energy requirement of inactive cats (kcal/d)=50×BW (kg), whilst energy requirement of active cats (kcal/d)=70×BW (kg).

Whilst the effect of different activity levels on energy requirement (and consequently feeding guides) can be accounted for (as above), other factors that influence energy requirements cannot be so easily accounted for using existing methods. In particular body composition or the proportion of fat and fat free mass (or lean tissue) are important factors influencing an individuals energy requirement. Fat free tissue (or lean tissue) is metabolically active whilst fat tissue is not. Energy requirements are therefore determined by the mass of metabolically active tissue (represented by fat free or lean tissue mass) and not by the amount of fat tissue.

Current methods for estimating energy requirements assume that the energy requirement is fixed at a given body weight. However this approach can overestimate energy requirements in certain individuals. For example, in overweight cats lean tissue (or fat free tissue) accounts for a lower proportion of body weight than in cats of normal body weight. Consequently the energy requirement per unit body weight of overweight cats will be less than that of normal weight cats. As lean tissue is metabolically active and fat tissue is not, cats which are overweight are likely to be offered excessive energy if fed at an energy requirement which is fixed at a given body weight.

This risk of over feeding obese cats was highlighted in a recent study which showed that the mean daily energy requirement of eight obese adult cats (47.74±2.41% fat) was significantly (P<0.05) lower than a group of non-obese (26.05±1.61% fat) age and sex matched cats, when compared on a kg body weight basis (33±2% cal/kg BW and 43±2 kcal/kg BW respectively). However, when this energy requirement is expressed on a lean mass basis (the proportion of body composition which is considered to be metabolically active) there is no difference between the two groups (67±2 and 60±2 kcal/kg lean mass respectively, P>0.05).

Feeding the obese cats at a fixed energy requirement for a given body weight would therefore result in an excessive energy allowance and could result in increasing fatness.

Fat free mass (FFM) consists predominantly of lean mass (approx. 97%) and a small amount of bone mineral content. Therefore, expressing energy requirement on a FFM basis will give more accurate feeding guides because it removes the influence of fat mass. Fat free mass can be determined from the weight of the cat and the percentage body fat content of the animal which can be obtained from the feline body mass index (FBMI) (equation 1).

FFM=Body weight (kg)×([100−% Body fat]/100)  Equation 1

The % Body fat could be determined from the Feline Body Mass Index discussed above, or by another method.

The FFM can be converted to an "ideal" body weight (equation 2) which determines the mass of the cat with an optimal body composition (Table 1). Data collected a. WCPN showed that cats with an optimal body condition had a body fat content of approximately 25%.

"Ideal" weight=FFM×1.33  Equation 2

The "ideal" weight is the weight at which a cat is neither under or over weight, and can be used as a target weight.

There was no significant difference between the obese and non-obese cats in their energy requirement per kg "ideal" weight (48±2 and 44±2 kcal/kg "ideal" weight respectively), demonstrating that feeding guides based upon "ideal" weight could be more useful than the current ones based upon body weight alone, because they take into account body composition (Table 2, 3). In addition, "ideal" weight could also be used to determine target weight and energy requirements for cats under-going weight loss (Table 4).

The optimal body condition of 25% fat was determined by repeated imperial measurements and observation. The energy requirements per kg "ideal" weight were also determined by observation.

What is claimed is:

1. A method for determining the percentage body fat of a four legged domestic pet mammal, comprising the steps of:
   measuring a first body dimension having a high correlation with percentage body fat;
   measuring a second body dimension having a low correlation with percentage body fat; and
   determining the percentage body fat from a relationship between only the first and second body measurements and the percentage body fat using a body fat look-up table comprising a first storage area for storing therein entries of the first body dimension, a second storage area storing therein entries of the second body dimension and an output storage area storing an indication of the percentage body fat.

2. A method according to claim 1, wherein the first body measurement is the circumference of the ribcage, taken at the $9^{th}$ rib.

3. A method according to claim 1, wherein the second body measurement is a leg index measurement, which is the length of the hind limb measured between the patella (knee) and the calcaneal tuber (hock).

4. A method according to claim 1, wherein the output storage area provides an indication of whether the mammal is under, normal or overweight.

5. A method according to claim 1, wherein the output storage area provides a numerical percentage body fat.

6. A method according to claim 1, wherein the relationship between the percentage body fat and first and second body dimension is given by the equation:

$$PercentageBodyFat = \left[\frac{\left(\frac{R}{C_1} - L\right)}{C_2}\right] - L$$

where
R=ribcage circumference
L=leg index measurement

C1=constant

C2=constant.

7. A method according to claim 1, wherein the four legged mammal is a cat.

8. A method according to claim 1, comprising the further step of determining a target body weight from a relationship between the percentage body fat, a body weight and the target body weight using a look-up table comprising a first storage area for storing entries of the percentage body fat, a second storage area for storing entries of body weight, and an output storage area storing an indication of the target body weight.

9. A method according to claim 8, wherein the relationship between the target weight, the body weight and the percentage body fat is given by the equation:

$$\text{Target weight} = 1.33 \times \text{Body weight (kg)} \times ((100 - \% \text{ body fat})/100).$$

10. A method according to claim 8, wherein the target weight is an ideal weight.

11. A method according to claim 8, further comprising the step of determining an energy allowance.

12. A method according to claim 11, wherein the energy allowance is a daily allowance in kcal/kg.

* * * * *